US008775218B2

(12) United States Patent
Burgoon, Jr. et al.

(10) Patent No.: US 8,775,218 B2
(45) Date of Patent: Jul. 8, 2014

(54) TRANSFORMING DATA FOR RENDERING AN INSURABILITY DECISION

(75) Inventors: J. David Burgoon, Jr., Weldon Spring, MO (US); David L. Snell, Chesterfield, MO (US); Susan L. Wehrman, Ballwin, MO (US)

(73) Assignee: RGA Reinsurance Company, Chesterfield, MO (US)

( * ) Notice: Subject to any disclaimer, the term of this patent is extended or adjusted under 35 U.S.C. 154(b) by 77 days.

(21) Appl. No.: 13/274,869

(22) Filed: Oct. 17, 2011

(65) Prior Publication Data

US 2012/0296676 A1 Nov. 22, 2012

Related U.S. Application Data

(60) Provisional application No. 61/487,562, filed on May 18, 2011.

(51) Int. Cl.
*G06Q 40/00* (2012.01)
(52) U.S. Cl.
USPC .............................................................. 705/4
(58) Field of Classification Search
USPC ................................................. 705/4, 35–45
See application file for complete search history.

(56) References Cited

U.S. PATENT DOCUMENTS

| 5,191,522 | A | | 3/1993 | Bosco et al. | |
| 5,307,262 | A | * | 4/1994 | Ertel | 705/2 |
| 5,930,762 | A | | 7/1999 | Masch | |
| 6,110,109 | A | | 8/2000 | Hu et al. | |
| 6,802,810 | B2 | | 10/2004 | Ciarniello et al. | |
| 7,233,938 | B2 | | 6/2007 | Carus et al. | |
| 7,383,239 | B2 | * | 6/2008 | Bonissone et al. | 706/46 |
| 7,555,439 | B1 | | 6/2009 | Binns et al. | |
| 7,617,169 | B1 | | 11/2009 | Owen et al. | |
| 7,707,169 | B2 | | 4/2010 | Comaniciu et al. | |
| 7,711,660 | B1 | * | 5/2010 | Gentile et al. | 706/8 |
| 7,756,728 | B2 | | 7/2010 | Maughan et al. | |
| 7,801,748 | B2 | * | 9/2010 | Bonissone et al. | 705/4 |

(Continued)

FOREIGN PATENT DOCUMENTS

| TW | 554276 B | 9/2003 |
| WO | 0141019 A2 | 6/2001 |
| WO | 02084520 A1 | 10/2002 |
| WO | 2005017701 A2 | 2/2005 |

OTHER PUBLICATIONS

"Protection: Underwriting success", Money Marketing, Feb. 19, 2004, p. 54.*

(Continued)

*Primary Examiner* — Mohammad Z Shaikh
(74) *Attorney, Agent, or Firm* — Senniger Powers LLP

(57) ABSTRACT

Transformation of disparate data for use in rendering a decision involving a potentially insurable risk. An Extract, Transform, Load (ETL) process extracts the data and converts it from a plurality of formats into a standard format for processing. A heuristic engine inferentially processes the converted data to identify information relevant to the decision to be rendered. A consolidation and presentation engine generates presentable knowledge from the relevant information and then presents the knowledge to a decision-making entity for rendering the decision. And an optimization feedback process monitors one or more actions on the presented knowledge by the decision-making entity and adjusts one or more of the ETL process, the heuristic engine, and the consolidation and presentation engine as a function of the monitored actions.

22 Claims, 6 Drawing Sheets

(56) References Cited

U.S. PATENT DOCUMENTS

| | | | |
|---|---|---|---|
| 7,802,183 B1 | 9/2010 | Essin | |
| 7,813,945 B2* | 10/2010 | Bonissone et al. | 705/4 |
| 7,818,186 B2* | 10/2010 | Bonissone et al. | 705/4 |
| 7,822,626 B2 | 10/2010 | Harp et al. | |
| 7,823,207 B2* | 10/2010 | Evenhaim | 726/26 |
| 7,844,476 B2* | 11/2010 | Bonissone et al. | 705/4 |
| 7,844,477 B2* | 11/2010 | Bonissone et al. | 705/4 |
| 7,865,375 B2 | 1/2011 | Lancaster et al. | |
| 7,895,062 B2* | 2/2011 | Bonissone et al. | 705/4 |
| 7,895,064 B2 | 2/2011 | Wahlbin | |
| 7,899,688 B2* | 3/2011 | Bonissone et al. | 705/4 |
| 8,005,693 B2* | 8/2011 | Bonissone et al. | 705/4 |
| 8,073,716 B2* | 12/2011 | Pelenur et al. | 705/4 |
| 8,073,717 B2* | 12/2011 | Pelenur et al. | 705/4 |
| 8,214,314 B2* | 7/2012 | Bonissone et al. | 706/46 |
| 8,332,243 B2* | 12/2012 | Brzezicki et al. | 705/4 |
| 2001/0053986 A1 | 12/2001 | Dick | |
| 2002/0138307 A1* | 9/2002 | Kramer | 705/4 |
| 2003/0046113 A1 | 3/2003 | Johnson et al. | |
| 2005/0102159 A1 | 5/2005 | Mondshine | |
| 2005/0187794 A1 | 8/2005 | Kimak | |
| 2005/0192838 A1 | 9/2005 | Jones et al. | |
| 2005/0203892 A1 | 9/2005 | Wesley et al. | |
| 2005/0234740 A1 | 10/2005 | Krishnan et al. | |
| 2005/0288971 A1 | 12/2005 | Cassandra | |
| 2006/0004745 A1 | 1/2006 | Kuhn et al. | |
| 2006/0095298 A1 | 5/2006 | Bina | |
| 2006/0100912 A1 | 5/2006 | Kumar et al. | |
| 2006/0293920 A1 | 12/2006 | Stroup et al. | |
| 2007/0055552 A1 | 3/2007 | St. Clair et al. | |
| 2007/0078687 A1 | 4/2007 | Dettinger et al. | |
| 2007/0178501 A1 | 8/2007 | Rabinowitz et al. | |
| 2007/0276851 A1 | 11/2007 | Friedlander et al. | |
| 2007/0299760 A1* | 12/2007 | Lange et al. | 705/36 R |
| 2008/0104104 A1 | 5/2008 | Nolan et al. | |
| 2008/0154651 A1 | 6/2008 | Kenefick et al. | |
| 2008/0281631 A1 | 11/2008 | Syth et al. | |
| 2009/0024414 A1 | 1/2009 | Mansour et al. | |
| 2009/0119133 A1 | 5/2009 | Yeransian et al. | |
| 2009/0164249 A1 | 6/2009 | Hunt et al. | |
| 2009/0326983 A1 | 12/2009 | Kunz | |
| 2009/0326987 A1* | 12/2009 | Roudaut | 705/4 |
| 2010/0082370 A1 | 4/2010 | Frederick et al. | |
| 2010/0223078 A1 | 9/2010 | Willis et al. | |
| 2011/0077977 A1* | 3/2011 | Collins et al. | 705/4 |
| 2011/0178902 A1* | 7/2011 | Imrey et al. | 705/30 |

OTHER PUBLICATIONS

Hyle, Regis, Robert, ". . . and Nothing But the Truth: With acess to more data than ever before, insurers are struggling to come up with what has been described as a single version of the truth", Techdecisions for Insurance (Sep. 2006), pp. 1-3.*

Ciardiello, Gary; McLeroy, David, "Predictive Modeling Comes to Life", Techdecisions for Insurance, Mar. 2011, pp. 1-3.*

Iyer, N. and Bonissone, P., Automated Risk Classification and Outlier Detection, IEEE Symposium on Computational Intelligence in Multicriteria Decsion Making, 2007, pp. 272-279.

Lee, R., Mark, K. and Chiu, D., Enhancing Workflow in Insurance Underwriting Processes with Web Services and Alerts, IEEE Department of Computing, 2007, pp. 1-9.

Meyer, M., Detore, A., Siegel, S. and Curley, K., The Strategic Use of Expert Systems for Risk Management in the Insurance Industry, ACM, 2007, pp. 551-572.

Pinpoint Solutions, Underwriting, retrieved from http://pinpnt/benefits/underwriting.html.

Underwriting for Medical Insurance, retrieved from http://www.sapiens.com/Medical-Underwriting.htm.

PCT International Search Report for PCT/US2012/034023 dated Mar. 13, 2013, 3 pages.

Written Opinion for PCT/US2012/034023 dated Mar. 13, 2013, 5 pages.

Kobielus, The Forrester Wave: Predictive Analytics and Data Mining Solutions, Q1 2010. Dated Feb. 4, 2010, 22 pages.

* cited by examiner

TRANSFORMING DATA FOR RENDERING AN INSURABILITY DECISION

BACKGROUND

Insurance companies typically determine insurance premiums and rates for applicants based on the process of underwriting. In other words, underwriting involves measuring risk exposure and determining the premium that needs to be charged to insure that risk. For example, life insurance underwriting involves determining an individual's relative mortality and health insurance underwriting involves determining an individual's relative morbidity. And as part of the underwriting process for life or health insurance, medical underwriting and other factors (e.g., age and occupation) are used to examine the applicant's health status.

Several sources of medical and nonmedical data exist for use in the underwriting process. For example, a life or health insurance company often has internal records from previous policies, application data for a currently proposed policy, and data available from external sources such as hospital and physician records, and prescription drug usage services. The hospital and physician data can take the form of Electronic Medical Records (EMR) or Patient Medical Information (PMI) files (including Attending Physician Statements (APS)). And commercial inspection companies make available to insurance companies a wide array of information from banking or financial information to driving history. To say this represents a river of data is an understatement. The insurance underwriter is faced with the task of drinking from the fire hose. Although most, but not all, of these disparate sources are developing emerging standards for this data, the standards for one source often vary widely from the standards for another source because each source is focused on satisfying a different business need.

Each insurance company has its own set of underwriting guidelines to help an underwriter determine whether or not the company should accept a risk and at what cost and with what restrictions. Once an applicant for insurance authorizes the company's access to various pieces of information, the underwriting process uses the information to evaluate the risk of the applicant for insurance based on the type of coverage involved. Insurance companies sometimes use automated underwriting systems to deliver an underwriting decision.

SUMMARY

Aspects of the invention translate and map data from a medical record or the like into a structured database to enable the data to be underwritten by either an electronic program or a human underwriter.

A method embodying aspects of the invention transforms disparate data for use in rendering a decision involving a potentially insurable risk. The method includes receiving data, which is in a plurality of formats, from a plurality of sources. The data is extracted and converted into one or more standard formats. The method also includes filtering the converted data by relevancy to the decision to be rendered, generating presentable knowledge from the converted data, and presenting the knowledge to a decision-making entity for rendering the decision. By monitoring one or more actions on the presented knowledge by the decision-making entity, the method can adjust one or more of steps as a function of the monitored actions.

In an aspect, a method of structuring and transforming disparate data for use in rendering a decision involving a potentially insurable risk includes retrieving data from a first database and transforming the retrieved data into domain-specific information. Once transformed, the information, which relates to the potentially insurable risk, is stored in a second database. The method includes defining one or more relevancy factors as a function of the decision to be rendered and assigning at least one of the relevancy factors to at least a portion of the information stored in the second database. Additionally, the method includes providing an output of the second database with the assigned relevancy factors to a decision-making entity for rendering the decision.

In another aspect, a computer-readable medium stores computer-executable instructions that, when executed, transform disparate data for use in rendering a decision involving a potentially insurable risk. The computer-readable medium comprises, data from a plurality of sources and in a plurality of formats, an Extract, Transform, Load (ETL) process, a heuristic engine, a consolidation and presentation engine, and an optimization feedback process. The ETL process extracts the data and converts it from the plurality of formats into one or more standard formats. The heuristic engine inferentially processes the converted data to identify information relevant to the decision to be rendered. The consolidation and presentation engine generates presentable knowledge from the relevant information and then presents the knowledge to a decision-making entity for rendering the decision. And the optimization feedback process monitors one or more actions on the presented knowledge by the decision-making entity and adjusts one or more of the ETL process, the heuristic engine, and the consolidation and presentation engine as a function of the monitored actions.

In yet another aspect, a system includes a memory storing disparate data relating to a potentially insurable risk. A computer executes a process for extracting at least a portion of the stored data and transforming the extracted data from a plurality of formats into a standardized format. The memory then stores the transformed data in the standardized format. The computer executes a heuristic engine for analyzing the transformed data for relevancy to a decision to be rendered involving the potentially insurable risk. Moreover, the heuristic engine assigns one or more relevancy factors to the analyzed data. In addition, a display displays an output including the assigned relevancy factors to a decision-making entity for rendering the decision.

In an aspect of the invention, an automated system is capable of interpreting medical conditions presented in a structured medical record into one of a plurality of limited underwriting impairments. The automated system is user-configurable to include more or fewer underwriting impairments. And the automated system is user-configurable to enable modification of the medical condition mappings into underwriting impairments. The automated system includes the capability to translate, interpret, and map a known medical condition based on one or more factors including, but not limited to: medical condition name; medical condition code (e.g., CPT4, ICD9, ICD10, etc.); medications assigned; treatment regimens; age; gender; and so forth.

In another aspect, the automated system receives its input data from various sources such that the data received is in a structured data format capable of being interpreted by an automated system.

In yet another aspect, the automated system produces a structured data output consisting of at least one of the following: an underwriting medical condition; a severity indication; a recommended action; or an indication that the medical condition is referred to a human to correctly map the medical condition to an underwriting impairment.

In yet another aspect of the present invention, the output of the automated system is an input to an automated system or as input to a human for the actual process of underwriting the individual under consideration.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
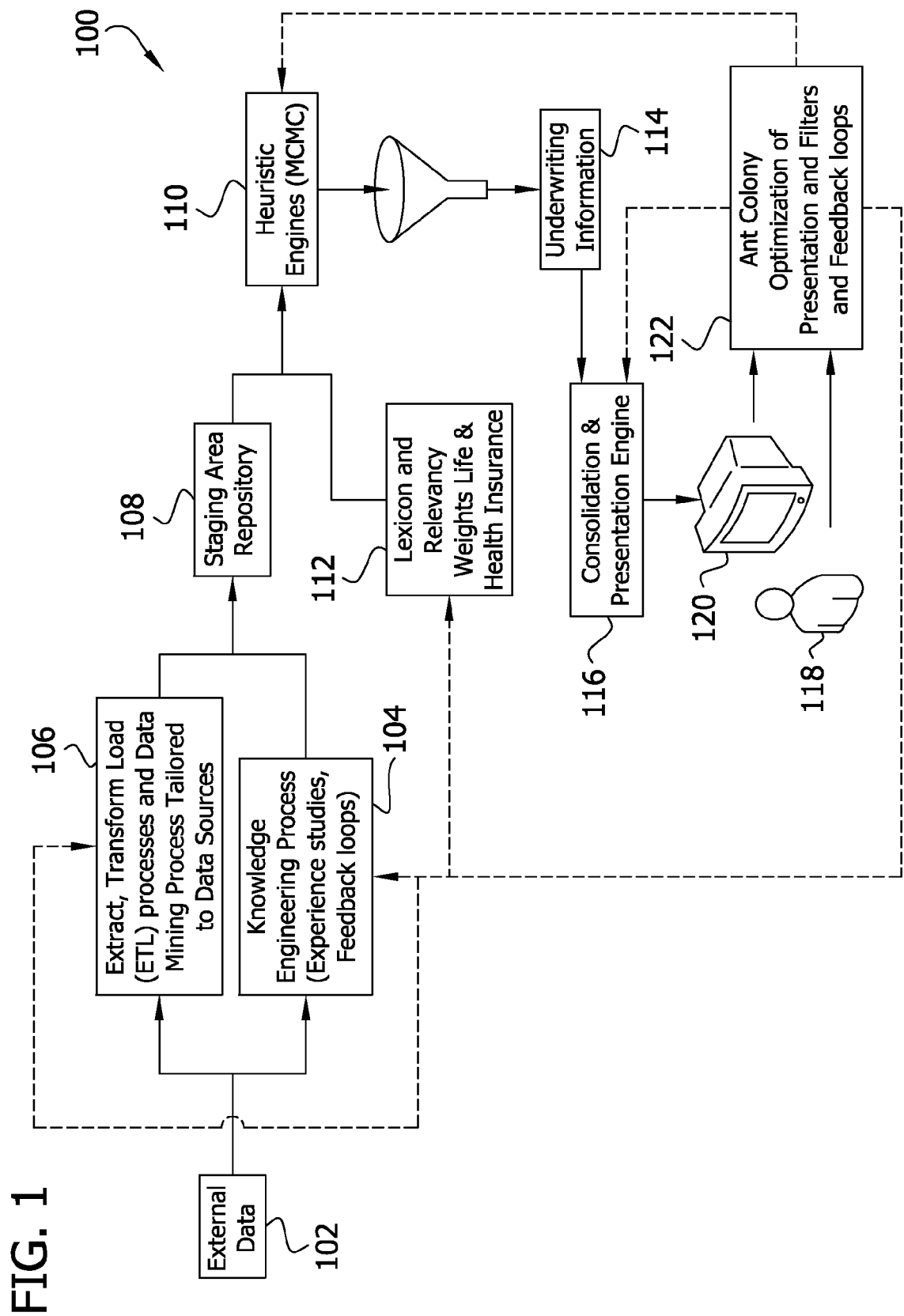
FIG. 1 is an exemplary block diagram illustrating a system for transforming medical and other data according to an embodiment of the invention.

Referring now to the figures, aspects of the present invention translate and map information about an insurance applicant into a structured database. This enables the information to be more effectively and efficiently underwritten by either an electronic program or a human underwriter. In one embodiment, a computer system, generally indicated at 100, receives information, such as data stored in an external data database 102, and creates structured data that fits into major "underwritten" sections (e.g., cardiovascular disease). The structured data is preferably used for further underwriting evaluation, either by an automated system or by a human underwriter.

As an example, the data stored in the external data database 102 comprises data from electronic medical records (EMRs). This external data can be from several sources and in varying formats. The system 100 evaluates each EMR, for example, to identify relevant information and to translate the identified information. In this regard, system 100 uses industry-wide classifications, performs lexical analysis, accesses open-source or propriety databases (e.g., databases provided by a reinsurance company), or the like. The EMR data input to system 100 often includes fields such as medical condition name, medical condition code, medications assigned, treatment regimens, age, gender, and so on.

As another example, a suitable source of information is a continuity of care record (CCR). Those skilled in the art are familiar with CCR standards for creation of electronic summaries of patient health. The CCR provides a means for a healthcare practitioner, system, or setting to aggregate pertinent data about a patient and forward it to another practitioner, system, or setting to support the patient's continuity of care. For example, a typical CCR includes a summary of the patient's health status (e.g., problems, medications, allergies, lab results, procedures) and basic information about insurance, advance directives, care documentation, and care plan recommendations. The CCR is not an EMR or electronic health record (EHR) but it often contains some of the same data as an EMR or EHR. A continuity of care document (CCD) is a CCR created under the Clinical Document Architecture (CDA) standard.

Aspects of the invention also relate to creating structured data from non-traditional records sources such as data from social networks and from internet datamarts instead of or in addition to EMR, EHR, CCR, and/or CCD data or the like.

An underwriting impairment typically defines factors that tend to increase an individual's risk above that which is normal. Underwriting manuals define one or more underwriting impairments or underwriting impairment groups. Information in the underwriting impairment may define, for example, the individual's relative mortality, morbidity, and/or longevity. Although described in the context of life or health underwriting, it is to be understood that aspects of the invention also apply to disability, long term care, and other forms of insurance underwriting.

As shown in FIG. 1, computer system 100 permits selection and mapping of translated external data from database 102 to a structured database. The external data stored in database 102 includes, for example, applicant-provided data, financial sources data, motor vehicle records data, other non-medical sources data, electronic medical records data, electronic health records data, continuity of care records or documents data, prescription data, and other medical sources data.

The system 100 first extracts relevant information from the external data and then converts the extracted data into standard formats for processing. In one embodiment, system 100 weighs, filters, or otherwise deems information to be more or less relevant based on factors such as source, type, age of data, covariance with other factors, etc. And the resulting structured data preferably contains fields such as an underwriting medical condition, a severity indication, a recommended action, and/or an indication that further manual review is desired or required.

In one embodiment of system 100, the application programs 36 (see FIG. 6) include a plurality of processes that when executed by system 100 filter the structured data by relevancy and mine the data for valuable information. The processes further convert this information into knowledge, namely, information that is particularly useful in the underwriting process. FIG. 1 shows at least one knowledge engineering process, generally indicated process 104 for determining which of the relevant information is actually usable in the underwriting process. Preferably, the process 104 employs experience studies, feedback, etc. to create and apply a knowledge model to the data. In addition, one or more extract, transform, load (ETL) processes and one or more data mining processes, generally indicated process 106, filter the structured data by relevancy and mine the data for valuable information. The result of these highly specialized processes 104, 106 is a relatively large staging area repository 108 of potentially usable data concerning the applicant.

At least one heuristic engine 110 analyzes staged data stored in the repository 108. In particular, the heuristic engine 110 compares the data against a proprietary database 112 representing a lexicon of phrases, synonyms, ICD 10 codes, etc. and the covariances of the data items. Moreover, engine 110 assigns relevancy weightings for life underwriting or for health underwriting. The output of heuristic engine 110 is a refined, filtered collection of information pertinent to the underwriting process stored in an underwriting information database 114.

In one embodiment, heuristic engine 110 executes a Markov Chaining Monte Carlo (MCMC) algorithm. Those skilled in the art are familiar with algorithms of this type for use in predictive modeling. Aspects of the present invention utilize the MCMC methodologies to infer risk assessment relationships in seemingly unrelated data from disparate sources.

At least one consolidation and presentation engine 116 presents the structured output of heuristic engine 110 in a form more directly usable for underwriting (either manual or automated or both). Moreover, the consolidation and presentation engine 116 offers a drill-down capability, described below, to further underwriting information stored in a database 114. In this manner, engine 116 outputs scenario and applicant-specific information as well as reference statistics particularly useful in the underwriting process.

Referring further to FIG. 1, system 100 includes a visual tool that enables a user, such as an underwriter 118, to view the information output from heuristic engine 110 as well as the information's underlying factors. Moreover, the visual tool enables the underwriter 118 access to the information in the underwriting information database 114. In one embodiment, the visual tool comprises a dashboard of consolidated summary information displayed on a display of a computer 120. The underwriter 118, generally considered the decision maker in underwriting scenarios, renders his or her decision based on the summary information. Typically, underwriter 118 is a trained professional who evaluates the presented data and makes a decision to approve the application at a specific rating for the policy, to decline the application, or to request more information. In an alternative embodiment, the computer 120 executes automated underwriting processes in addition to or instead of manual underwriting by underwriter 118. In the absence of a human underwriter, computer 120 constitutes the underwriter in this alternative embodiment.

In an embodiment, a feedback system based on the consumption or modification of the structured data is used to refine and adjust the selection, translation, and/or mapping of data to the structured database. Moreover, the feedback process monitors underwriter actions and results and alters previous operations via feedback loops. For example, the actions of each individual underwriter 118 are closely observed using an optimization technique, such as an "Ant Colony Optimization" technique executed at process 122. The process 122 infers collective information from the repeated and combined actions of independent individuals and adjusts the dashboard of summary information displayed at computer 120 accordingly.

Figure 2:
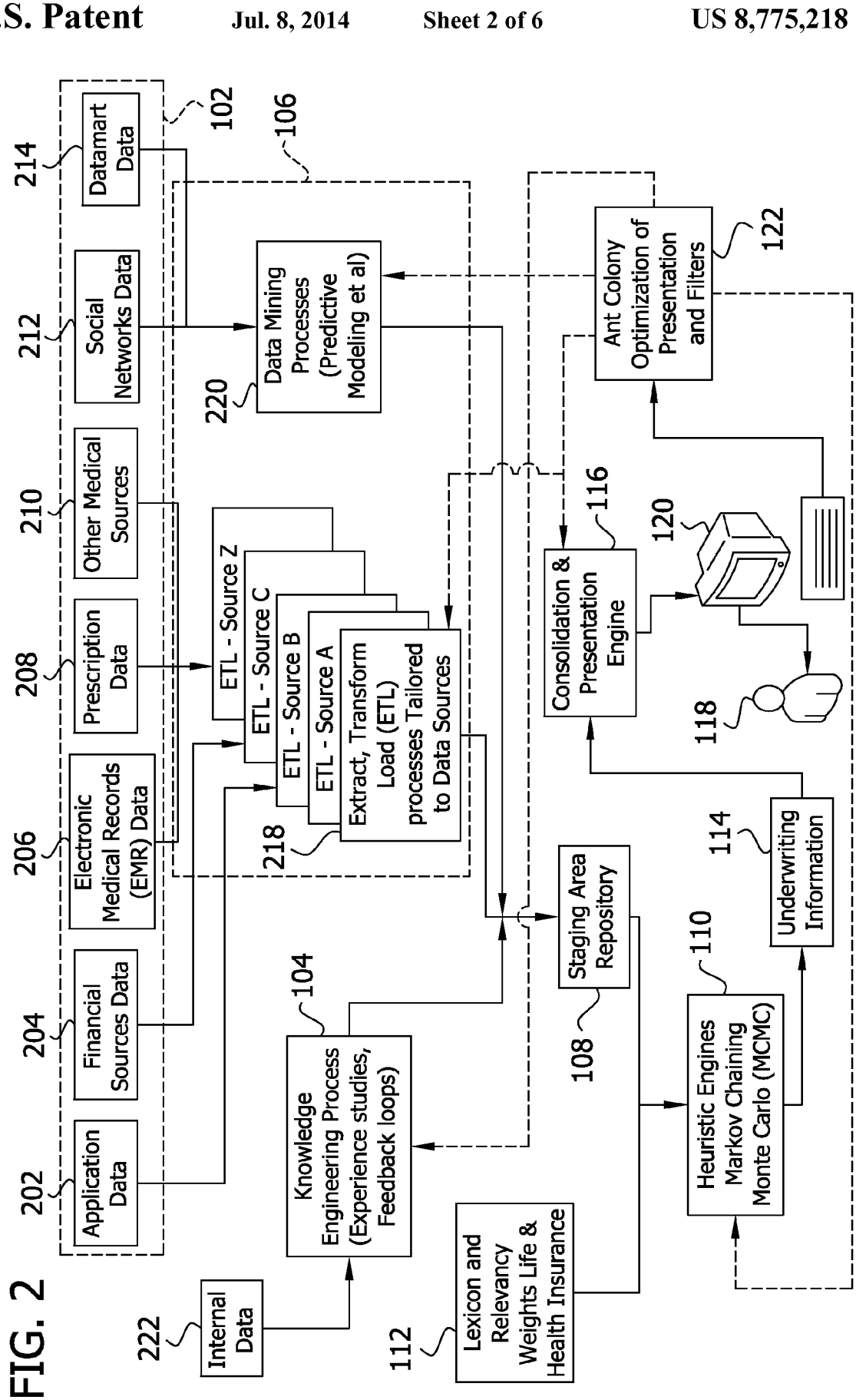
FIG. 2 is an exemplary block diagram illustrating a system for transforming medical and other data according to another embodiment of the invention.

FIG. 2 illustrates an alternative embodiment of the invention. As shown in FIG. 2, computer system 100 permits selection and mapping of translated external data stored in database 102 to a structured database. The external data 102 includes, for example, applicant-provided data 202, financial sources data 204, electronic medical records data 206, prescription data 208, and other medical sources data 210 (including but not limited to, for example, continuity of care records data). In addition, external data database 102 includes complex data from non-EMR sources such as social network data 212 and internet datamart data 214. The different types of external data included in the external data database 102 can be stored in one or more database structures.

Advantageously, extracting information from multiple data sources provides the benefit of network theory. In this regard, the strength of a network is the usual fault tolerance (e.g., random hits can take out as many as 80% of the locations while retaining functionality). But the weakness of a network is the vulnerability to catastrophe (e.g., targeted hits take out very few locations but cause chaos). The government sponsored movement towards more integration of medical and related information into personal medical records is countered to some extent by another regulatory initiative concerning privacy issues. The goals are at times in conflict and the posture regarding what information is fair game for risk assessments is in a state of flux. Embodiments of the invention use network theory to adjust processing centers for high efficiency of data processing and embracing of data deemed relevant, ethical, and legal to use, yet reduce the vulnerability to any specific data source or selection criterion as perspectives change.

The system 100 preferably uses inferential analysis to extract useful information from the external data. Those skilled in the art are familiar with computational methods such as predictive modeling, Bayesian inference, genetic algorithms, and the like for performing inferential analysis. The system 100 first extracts relevant information from external data stored in database 102 and then converts the extracted data into a standard format for processing. In one embodiment, system 100 weighs, filters, or otherwise deems information to be more or less relevant based on factors such as source, type, age of data, covariance with other factors, etc. And the resulting structured data preferably contains fields such as an underwriting medical condition, a severity indication, a recommended action, and/or an indication that further manual review is desired or required.

Similar to the embodiment of FIG. 1, application programs 36 (see FIG. 6) include a plurality of processes that when executed by system 100 filter the structured data by relevancy and mine the data for valuable information. The processes further convert this information into knowledge, namely, information that is particularly useful in the underwriting process. FIG. 2 shows a plurality of processes, such as knowledge engineering process 104, heuristic engine 110, and consolidation and presentation engine 116. Moreover, FIG. 2 illustrates process 106 as one or more ETL processes 218 and one or more data mining processes 220. The processes 104, 106 (including 218, 220), 110, 116 are collectively referred to as inference engines.

The engine 116 transforms information from various sources into a form more directly usable for underwriting (either manual or automated or both). Traditional information sources include applicant-provided data 202, financial sources data 204, electronic medical records data 206, prescription data 208, and other medical sources data 210. The traditional sources of data, although different from each other in many respects, share a general perspective on the health or financial state of the applicant.

A person who recently underwent major surgery, or who is in financial distress, for example, is more likely to have a greater mortality or health insurance risk than another person with a secure, comfortably high income, low debt, good family history of longevity, lower (but not too low) blood pressure and cholesterol levels, and a body mass index (BMI) and other physical characteristics in the more desirable ranges.

The consolidation and presentation engine 116 generates succinct, high usable information from the transformed data stored in underwriting information database 114. For example, engine 116 summarizes data representing years of biometric levels into a moving weighted average. In another embodiment, engine 116 presents a chart of the metrics superimposed on a background chart of those metrics for the normal range of individuals of similar age, gender, smoker status, and other key underwriting criteria. Similarly, instead of data representing years of prescriptions, engine 116 presents a listing of the distinct prescriptions, and an indication of dosage levels (and increasing or decreasing trends), periods of noncompliance, and other key indicators to flag possible interactions between prescriptions or possible misuse of them.

In an alternative embodiment, engine 116 may be configured to operate on non-traditional information, such as social network data 212 and internet datamart data 214. Vast amounts of data on our personal lifestyle habits have been collected and stored in various datamarts. And people contribute to the collective knowledge by voluntary participation in social networks. Referring further to FIG. 2, if the traditional sources form a river, the social networks data 212 and associated datamarts data 214 (e.g., specialty companies that harvest data about us from myriad sources) form a sea of data. If processed effectively, this lifestyle data can be a useful prognosticator of future, rather than just current morbidity and mortality concerns. And this data could add significantly to the total picture of insurability.

For example, assume person X lives in a neighborhood where the crime rate is very low, jogging trails are plentiful, and the local culture encourages walking rather than driving. Further, X has high equity in her home, a graduate degree in a high paying but relatively low stress profession, and does not subscribe to the premium cable television package (thus, is not a couch potato). Instead, she subscribes to a popular magazine for serious runners, writes a blog on organic foods, buys mostly whole grains and vegetables on her loyalty card at the grocery chain, wrote a review of her cardiac monitoring wristwatch on an online retailer's website, regularly attends a yoga class at her local fitness center, and recently posted pictures to her social network profile showing her grandfather's 100th birthday celebration. This mix of data could provide a favorable indicator of X living for a longer time than an otherwise similar individual who posts, for example, pictures from a party at a local tavern, blogs about the taste differences of cigar A versus cigar B, and comments about recently buying a new muscle car to race at the local stock car track.

Today's life or health insurance underwriter is a magnificent human inference engine capable of assimilating information about an applicant and assigning appropriate risk classifications that drive the issuance of profitable, yet equitable, rates for insurance coverage. But it is no longer humanly possible (and certainly not cost effective) for an underwriter to study all of the data available for an applicant for a life or health insurance policy. Aspects of this invention embody a transformation from vast amounts of data to usable nuggets of information.

Referring further to FIG. 2, some data, especially data from the more traditional sources, are run through tailored ETL processes 218 to consolidate them into the common repository 108 for further study. In one embodiment, a tailored ETL process 218 corresponds to each source of external data 102. In other words, each ETL process 218 is specific to the domain, or source, of the data. The ETL process extracts information from its corresponding data source without regard to each data organization/format and transforms, or converts, the extracted data to a standard format. This permits consolidation and loading of the data into repository 108.

Other data, such as social networks data 212 and datamarts data 214, can be so voluminous as to make this more direct type of mapping process unfeasible in realistic timeframes. This other data 212, 214 is processed by, for example, advanced statistical methodologies, i.e., data mining processes 220. In one embodiment, data mining processes 220 comprise predictive modeling and similar techniques to "follow the bread crumbs" and detect covariance relationships between seemingly independent pieces of data.

The system 100 also operates on internal information stored in a database 222 and converts the raw data into a form more directly usable for underwriting. For example, a reinsurance company has a perspective on underwriting practices and mortality results across many companies and maintains its own repository of extensive data, indicated generally as internal data database 222. The knowledge engineering process 104 with expert human underwriters, actuaries, and other insurance professionals continually refines this valuable source of proprietary information.

Embodiments of the invention involve the storage of vast amounts of data, such as external data in database 102 (both traditional and non-traditional sources), internal data in database 222, lexicon and relevancy weights data in database 112, staged data in repository 108, and underwriting information in database 114. Although referred to as stored in databases or repositories, it is to be understood that the data can be stored, organized, and maintained in myriad forms.

In the embodiment of FIG. 2, heuristic engine 110 analyzes the staged data in repository 108. In particular, heuristic engine 110 compares the data against the proprietary database 112 representing a lexicon of phrases, synonyms, ICD 10 codes, etc. and the covariances of the data items. Moreover, engine 110 assigns relevancy weightings for life underwriting or for health underwriting.

For example, the relevancy of an item such as back pain might be of little consequence for a life application but of much higher relevance for health underwriting. And in another example, a hearing loss might be unimportant for most life applicants, yet rise in importance considerably if the applicant is employed as a traffic guard.

The result of this proprietary filtering process is a refined collection of information pertinent to life (or health, if that is the coverage sought) underwriting. Even this may be too much information for an underwriter to efficiently absorb. For example, BMI and blood pressure and cholesterol levels for the past 30 years is likely to be more information than underwriter 118 can effectively process. Similarly, information about monthly prescription medications for the past 15 years is likely too much data to be usable. The consolidation and presentation engine 116 transforms this information into a form more directly usable by the underwriter.

Referring further to FIG. 2, system 100 includes a visual tool that enables underwriter 118 access to the information in the underwriting information database 114. And in an embodiment, a feedback system based on the consumption or modification of the structured data is used to refine and adjust the selection, translation, and/or mapping of data to the structured database. Moreover, the feedback process monitors underwriter actions and results and alters previous operations via feedback loops. For example, the actions of each individual underwriter 118 are closely observed using an optimization technique, such as an "Ant Colony Optimization" technique executed at process 122. The process 122 infers collective information from the repeated and combined actions of independent individuals and adjusts the dashboard of summary information displayed at computer 120 accordingly.

For example, if multiple underwriters 118 tend to drill down on the medications and consult a dictionary for potential drug interactions, this becomes part of the collective knowledge of the inference engines 104, 218, 220, 110, and/ or 116. Future summary dashboards reflect this feedback by including this specific information, which saves underwriting time on future applications. Likewise, the information value is quickly scored by underwriter 118 and information used less frequently loses prominence, or real estate, on the summary screen. In this manner, aspects of the invention improve at providing the information wanted and not providing the extraneous data that obscures a cost and time effective decision on the part of the human expert. Likewise, if the information in the refined repository of underwriting information 114 is not sufficient, the inference engines 104, 218, 220, 110, and/or 116 may be adjusted accordingly.

Figure 3:
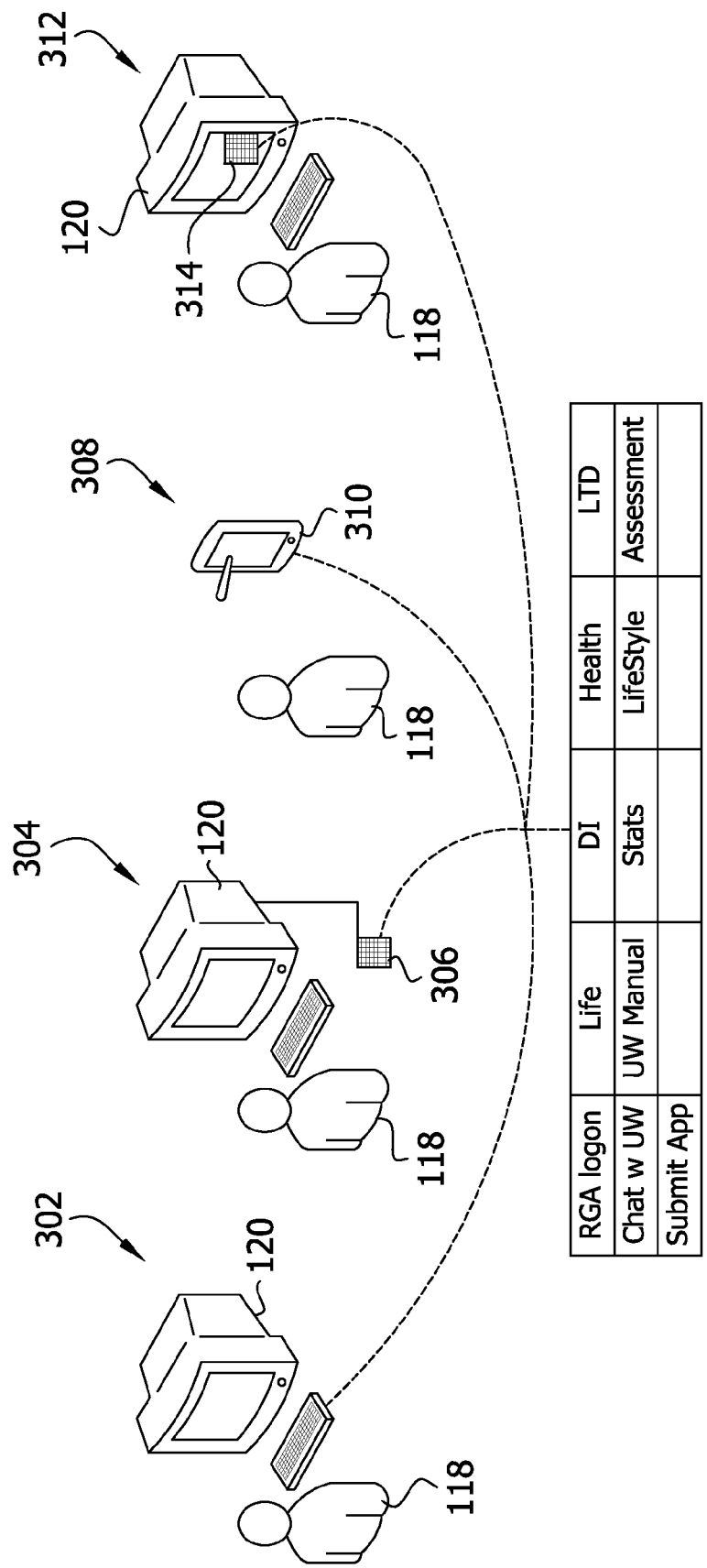
FIG. 3 is an exemplary block diagram illustrating alternative data sources to the system of FIGS. 1 and 2.

Aspects of the invention provide all that is necessary and sufficient without the distraction of that which is superfluous. And, in one embodiment, the invention comprises an underwriting appliance that has several alternative physical forms. Referring now to FIG. 3, a ceding company can choose a stand-alone, proprietary terminal linked to a reinsurer for maximum efficiency of this operation, or one of various other options that permit a balance of functionality and ease-of-use versus ceding company internal data security concerns.

For example, in FIG. 3, an underwriting appliance 302 (i.e., a hardware arrangement) comprises a dedicated terminal to the reinsurer, such as computer 120, with a specialized keyboard and hot keys to most common functions. This has no connection to ceding company IT operations and, thus, is ideal for situations where security is a prime concern of the ceding company. In an alternative underwriting appliance 304, the ceding company underwriter 118 uses a personal computer, such as computer 120, with a reinsurer specialized keypad 306 attached via the USB port or the like. This permits normal access to the ceding company network and peripherals. Moreover, the appliance 304 is convenient for a large underwriting department and for situations involving remote underwriters. Another alternative underwriting appliance 308 includes a specialized tablet 310 (e.g., an iPad) for use by a highly mobile underwriter 118. In yet another alternative underwriting appliance 312, the ceding company underwriter 118 uses a personal computer, such as computer 120, with no attached hardware. A relatively small, on-screen keyboard 314 is available to provide the hot key operations. This permits normal access to the ceding company network and peripherals. Similar to the underwriting appliance 304, the appliance 312 is convenient for a large underwriting department and for situations involving remote underwriters. Preferred hot keys on the specialized input device include an automatic login to the reinsurer's underwriting appliance via a secure internet site, and various views (arrangements of content and form) for differing benefit underwriting perspectives such as Life, Health, Disability Income, Long Term Care, etc. as well as direct access to the reinsurer's underwriting manual. Additional features include the ability to submit the application to the reinsurer.

Figure 4:
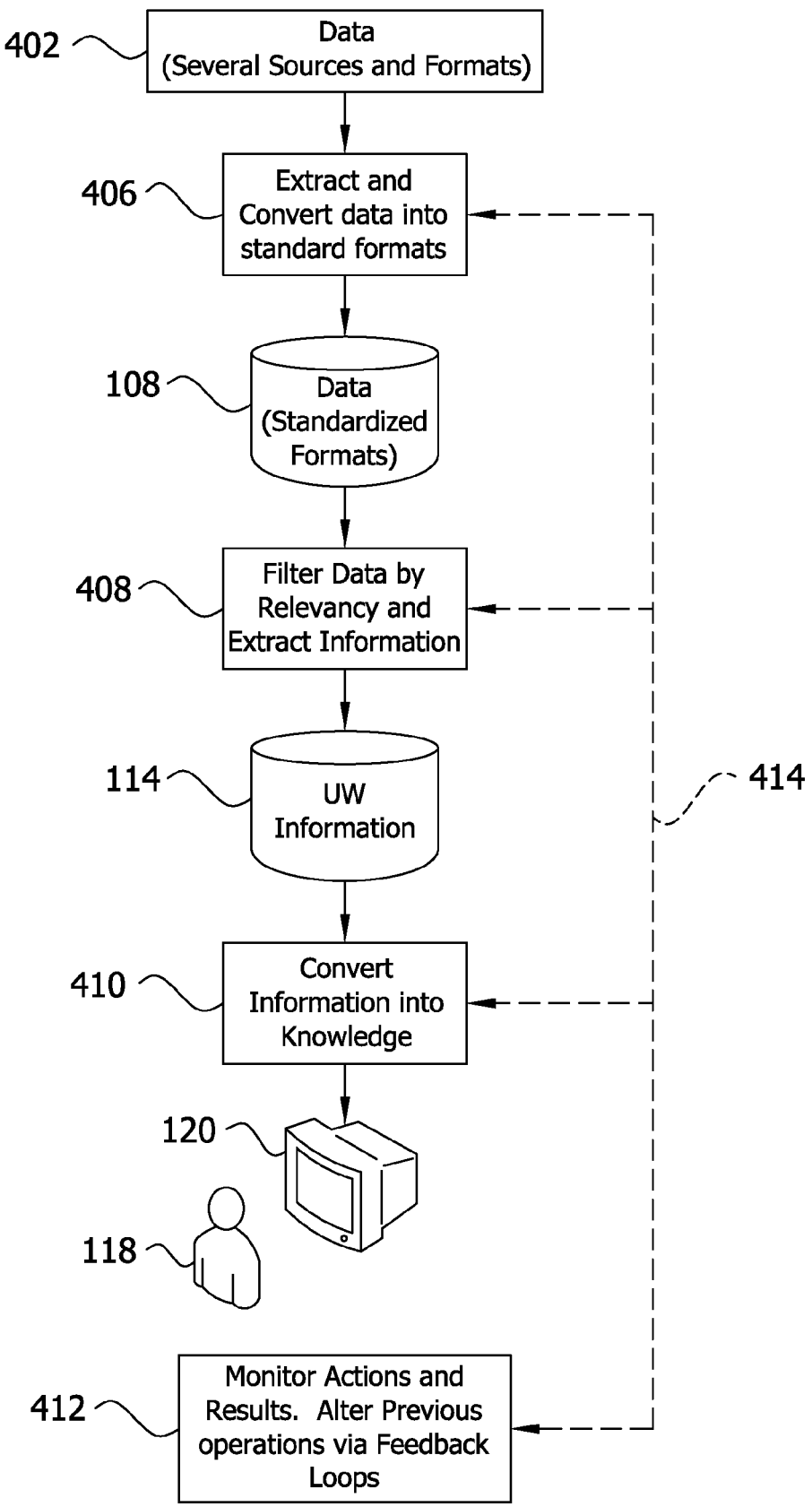
FIG. 4 is an exemplary flow diagram illustrating operation of the system of FIGS. 1 and 2.

FIG. 4 illustrates an exemplary, non-limiting process in accordance with an embodiment of the invention. In operation, computer system 100 receives external data 102 at 402 for selection and mapping to a structured database. As set forth above, external data 102 includes data from multiple sources in a variety of formats, such as applicant-provided data, financial sources data, electronic medical records data, prescription data, and other medical sources data. At 406, system 100 first extracts relevant information from external data 102 and then converts the extracted data into standard formats for processing. In one embodiment, system 100 executes process 104 and/or process 106 to perform the data extraction and conversion. The system 100 stores the extracted data in staging area repository 108.

Proceeding to 408, system 100 executes heuristic engine 110 to weigh, filter, or otherwise deem information to be more or less relevant based on factors such as source, type, age of data, covariance with other factors, etc. And the resulting structured data preferably contains fields such as an underwriting medical condition, a severity indication, a recommended action, and/or an indication that further manual review is desired or required. Moreover, engine 110 assigns relevancy weightings for life underwriting or for health underwriting. The output of heuristic engine 110 is a refined, filtered collection of information pertinent to the underwriting process stored in underwriting information database 114.

At 410, the consolidation and presentation engine 116 of system 100 converts this information into knowledge, namely, information that is particularly useful in the underwriting process. As a result, engine 116 presents the structured output of heuristic engine 110, i.e., the underwriting information 114, in a form more directly usable for underwriting (either manual or automated or both). The system 100 includes a visual tool that enables underwriter 118 to view the summary information output from heuristic engine 110 as well as the information's underlying factors. For example, computer 120 displays a dashboard of consolidated summary information to underwriter 118.

Feedback at 412 based on the consumption or modification of the structured data refines and adjusts the selection, translation, and/or mapping of data to the structured database. Moreover, the feedback process monitors underwriter actions and results and alters previous operations via feedback loops 414.

Figure 5:
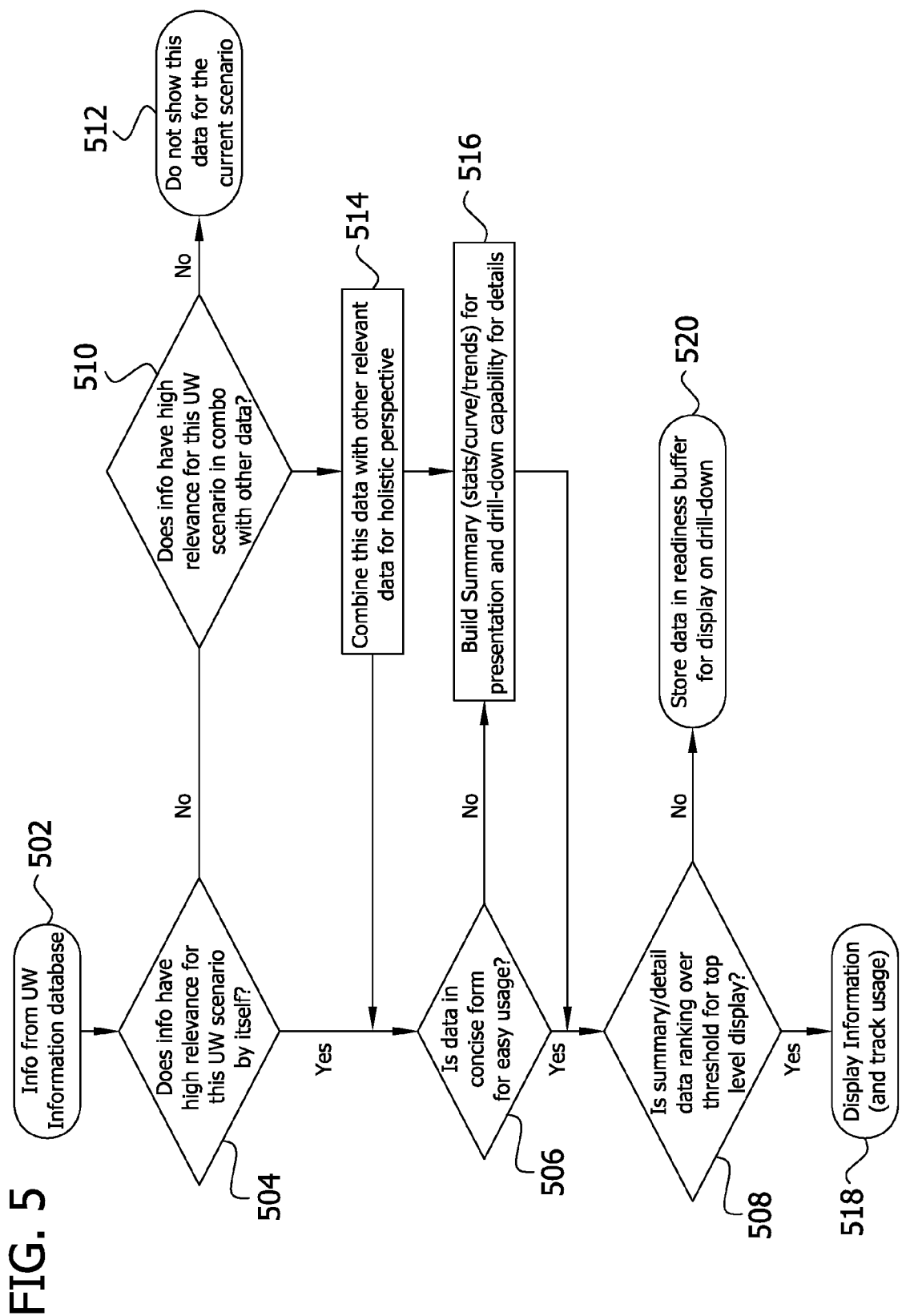
FIG. 5 is an exemplary flow diagram illustrating operation of a consolidation and presentation engine of the system of FIGS. 1 and 2.

FIG. 5 provides a logical overview of the operation of consolidation and presentation engine 116 at step 410 of FIG. 4 according to an embodiment of the invention. Beginning at 502, engine 116 receives the extracted information stored in underwriting information database 114. At 504, engine 116 executes a decision operation to determine whether the received information has a relatively high degree of relevance to the particular underwriting scenario. If so, engine 116 proceeds to 506 for a determination of whether the information is already in a concise, usable form. And if the information is relevant and concise, engine 116 determines at 508 whether the information is suitable for top level display.

On the other hand, if engine 116 determines at 504 that the received information does not have a sufficiently high degree of relevance to the particular underwriting scenario, operation proceeds to 510. At 510, engine 116 determines whether the information would have a relatively high degree of relevance if combined with other data. If not, the information engine 116 disregards the data at 512. But if the information would be sufficiently relevant if combined, engine 116 combines the data at 514 and proceeds to 506.

If engine 116 determines at 506 that the relevant information is not already in a concise, usable form, operation proceeds to 516. The engine 116 builds a summary at 516 such that the information is more usable in the underwriting process and then proceeds to 508 for a decision on whether the summarized information is suitable for top level display.

The engine 116 causes information suitable for top level display to be displayed at 518 and otherwise stores the information at 520 so that it is available for display when underwriter 118 drills down for further detail. The consolidation and presentation engine 116 offers the drill-down capability to permit underwriter 118 to access further underwriting information stored in a database 114. In other words, the relevance and nature of certain information may not warrant top immediate display but underwriter 118 can access the information if he or she deems it of importance to the underwriting decision. In this manner, engine 116 outputs scenario and applicant-specific information particularly useful in the underwriting process and provides the ability to drill down on additional underwriting information.

As described above, system 100 preferably uses inferential analysis to extract useful information from external data 102. The system 100 first extracts relevant information from external data 102 and then converts the extracted data into a standard format for processing. In one embodiment, system 100 weighs, filters, or otherwise deems information to be more or less relevant based on factors such as source, type, age of data, covariance with other factors, etc.

Those skilled in the art are familiar with computational methods such as predictive modeling, Bayesian inference, genetic algorithms, nature-inspired metaheuristic algorithms and the like suitable for performing inferential analysis in the form of knowledge engineering process 218, data mining process 220, heuristic engine 110, consolidation and presentation engine 116, and/or optimization process 122. Advantageously, system 100 according to an embodiment of the invention utilizes a combination of processes to weigh, filter, or otherwise deems information to be more or less relevant and to optimize the processes. This combination of processes permits system 100 to identify ways in which the processes are vulnerable to minute changes in data granularity, starting assumptions or on covariances between major and obscure variables, and adjust accordingly.

In the past, underwriters, actuaries, economists, and computer scientists built sophisticated mathematical models based upon prevailing reductionist theory, and expected the world to conform to them. They were dismayed when the world did not adhere and behave the way it was "supposed" to behave. In contrast, aspects of the present invention add the power of inductive reasoning techniques, which learn from the data and the way it is utilized. These adaptive aspects of the invention provide a unique advantage for the increasingly dynamic nature of risk assessment for life, health, disability income, long term care, and other types of insurance applications.

Aspects of the invention utilize complexity science tools and techniques, including predictive modeling, network theory, deterministic chaos, behavioral economics, fractal geometry, genetic algorithms, and cellular automata. These aspects represent a marked departure from the classical, more deterministic approach to risk assessment.

For example, embodiments of the invention involve the storage of vast amounts of data, such as external data in database 102 (both traditional and non-traditional sources), internal data in database 222, lexicon and relevancy weights data in database 112, staged data in repository 108, and underwriting information in database 114. Although vast, the data is readily accessible when needed, and the data models are highly scalable. In an embodiment, fractal geometry techniques help achieve scalability of interrelationship inferences beyond currently popular methods by taking advantage of self-similarities in the data.

In another example, genetic algorithms, namely, nature-inspired metaheuristic algorithms and the like, provide solutions to optimization and search problems in inferential analysis processes. Many risk assessment problems have no clear deterministic solution, and an exhaustive search is beyond computational capabilities. In a situation in which the number of variables (e.g., gender, age, height, weight, systolic and diastolic blood pressure readings, low and high density cholesterol readings, etc.) is large and the covariances of variables (such as diabetes plus high blood pressure plus obesity) can lead to complex interactions, system 100 in one embodiment uses one or more genetic algorithms to simulate emergent phenomena from the interactions of simpler, complex adaptive agents. An example of very simple agents interacting in complex ways would be the operation of an ant colony. An ant placed on a tabletop moves aimlessly but an ant colony is capable of complex behaviors even without a designated leader. In an analogous manner, ant colony optimizations, bee colony algorithms, and other modeling techniques based on the complex interactions of simple agents to solve problems not solvable with classic deterministic methods.

These nature-inspired metaheuristic algorithms are suited to observe the human actions of the underwriters as they utilize system 100. The dashboard output generated on computer 120 by consolidation and presentation engine 116 presents the information generally thought to be of the most interest to the human underwriter 118, with drill-down capability to get more granular or detailed information as desired. The feedback process monitors how often the various primary items are clicked for more information, and which items are ignored, or used less frequently. It will then spawn simulations to infer how the future dashboard arrangement can be changed to improve the user experience. The drill-down process also provides feedback to the collection and filtering routines (e.g., processes 104, 106) to ensure that desired information is collected and made more prominent. In a similar manner, ignored information no longer takes up valuable screen real estate (or in an extreme case, is no longer collected). It is contemplated that processes can evolve; and the continual application of scoring mechanisms to determine the "fittest" aspects of the process, coupled with the deliberately induced element of mutations (experimental features) can help system 100 to adapt to the changing scene of risk assessment in a manner superior to classical, more static, processes.

Moreover, it is contemplated that cellular automata principles can add a new dimension to genetic algorithm simulations for feedback and self-adjustment of the collection, filtering, relevancy, and presentation engine processes.

Embodiments of the present invention may comprise a special purpose or general purpose computer including a variety of computer hardware, as described in greater detail below.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage, or other magnetic storage devices, or any other medium that can be used to carry or store desired program code means in the form of computer-executable instructions or data structures and that can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such a connection is properly termed a computer-readable medium. Combinations of the above should also be included within the scope of computer-readable media. Computer-executable instructions comprise, for example, instructions and data which cause a general purpose computer, special purpose computer, or special purpose processing device to perform a certain function or group of functions.

Figure 6:
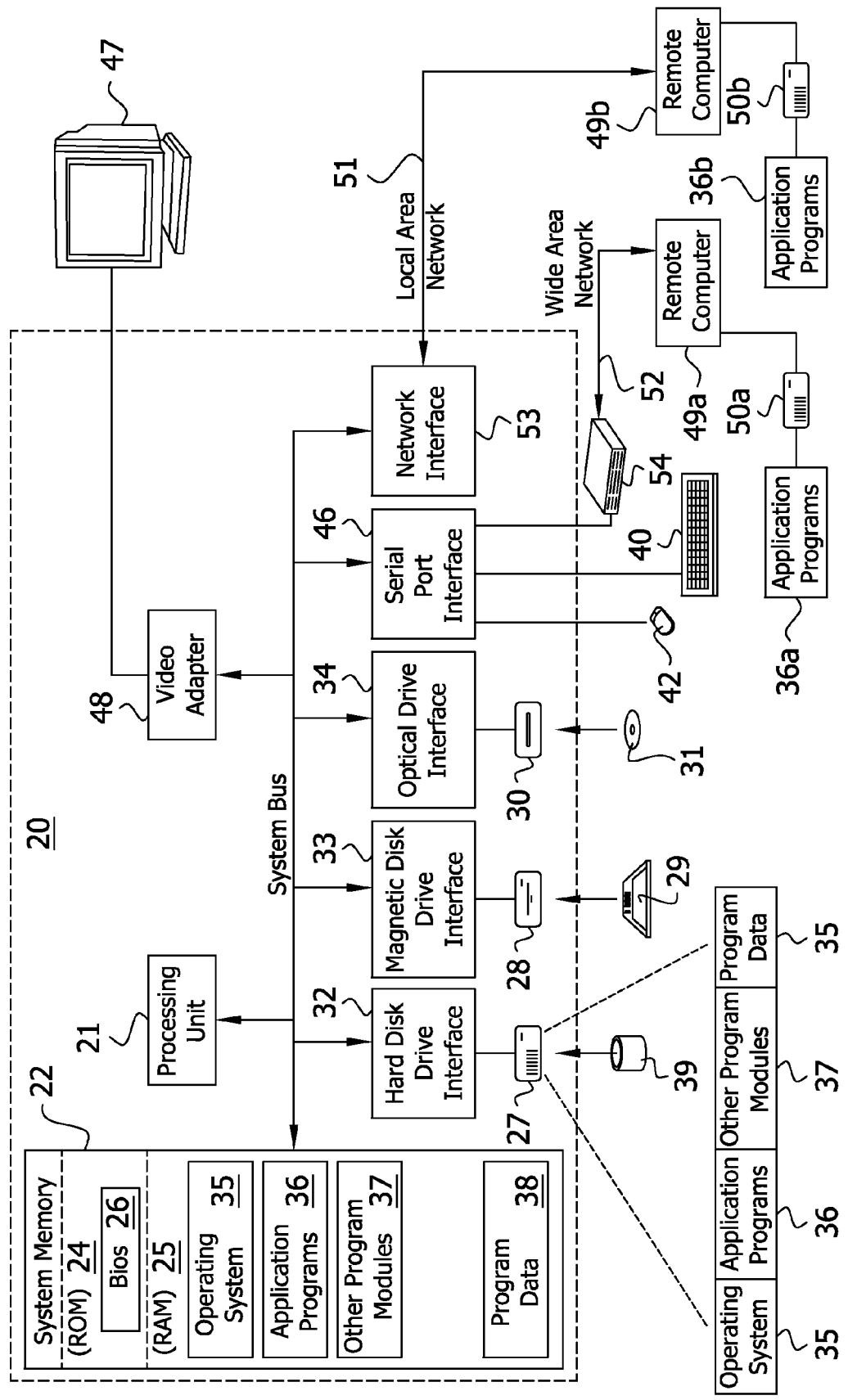
FIG. 6 is a block diagram illustrating an example of a suitable computing system environment in which aspects of the invention may be implemented.

FIG. 6 and the following discussion are intended to provide a brief, general description of a suitable computing environment in which aspects of the invention may be implemented. Although not required, aspects of the invention will be described in the general context of computer-executable instructions, such as program modules, being executed by computers in network environments. Generally, program modules include routines, programs, objects, components, data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represent examples of corresponding acts for implementing the functions described in such steps.

Those skilled in the art will appreciate that aspects of the invention may be practiced in network computing environments with many types of computer system configurations, including personal computers, hand-held devices, multi-processor systems, microprocessor-based or programmable consumer electronics, network PCs, minicomputers, mainframe computers, and the like. Aspects of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

With reference to FIG. 6, an exemplary system for implementing aspects of the invention includes a general purpose computing device in the form of a conventional computer 20, including a processing unit 21, a system memory 22, and a system bus 23 that couples various system components including the system memory 22 to the processing unit 21. The system bus 23 may be any of several types of bus structures including a memory bus or memory controller, a peripheral bus, and a local bus using any of a variety of bus architectures. The system memory includes read only memory (ROM) 24 and random access memory (RAM) 25. A basic input/output system (BIOS) 26, containing the basic routines that help transfer information between elements within the computer 20, such as during start-up, may be stored in ROM 24.

The computer 20 may also include a magnetic hard disk drive 27 for reading from and writing to a magnetic hard disk 39, a magnetic disk drive 28 for reading from or writing to a removable magnetic disk 29, and an optical disk drive 30 for reading from or writing to removable optical disk 31 such as a CD-ROM or other optical media. The magnetic hard disk drive 27, magnetic disk drive 28, and optical disk drive 30 are connected to the system bus 23 by a hard disk drive interface 32, a magnetic disk drive-interface 33, and an optical drive interface 34, respectively. The drives and their associated computer-readable media provide nonvolatile storage of computer-executable instructions, data structures, program modules, and other data for the computer 20. Although the exemplary environment described herein employs a magnetic hard disk 39, a removable magnetic disk 29, and a removable optical disk 31, other types of computer readable media for storing data can be used, including magnetic cassettes, flash memory cards, digital video disks, Bernoulli cartridges, RAMs, ROMs, and the like.

Program code means comprising one or more program modules may be stored on the hard disk 39, magnetic disk 29, optical disk 31, ROM 24, and/or RAM 25, including an operating system 35, one or more application programs 36, other program modules 37, and program data 38. A user may enter commands and information into the computer 20 through keyboard 40, pointing device 42, or other input devices (not shown), such as a microphone, joy stick, game pad, satellite dish, scanner, or the like. These and other input devices are often connected to the processing unit 21 through a serial port interface 46 coupled to system bus 23. Alternatively, the input devices may be connected by other interfaces, such as a parallel port, a game port, or a universal serial bus (USB). A monitor 47 or another display device is also connected to system bus 23 via an interface, such as video adapter 48. In addition to the monitor, personal computers typically include other peripheral output devices (not shown), such as speakers and printers.

The computer 20 may operate in a networked environment using logical connections to one or more remote computers, such as remote computers 49a and 49b. Remote computers 49a and 49b may each be another personal computer, a server, a router, a network PC, a peer device or other common network node, and typically include many or all of the elements described above relative to the computer 20, although only memory storage devices 50a and 50b and their associated application programs 36a and 36b have been illustrated in FIG. 6. The logical connections depicted in FIG. 6 include a local area network (LAN) 51 and a wide area network (WAN) 52 that are presented here by way of example and not limitation. Such networking environments are commonplace in office-wide or enterprise-wide computer networks, intranets and the Internet.

When used in a LAN networking environment, the computer 20 is connected to the local network 51 through a network interface or adapter 53. When used in a WAN networking environment, the computer 20 may include a modem 54, a wireless link, or other means for establishing communications over the wide area network 52, such as the Internet. The modem 54, which may be internal or external, is connected to the system bus 23 via the serial port interface 46. In a networked environment, program modules depicted relative to the computer 20, or portions thereof, may be stored in the remote memory storage device. It will be appreciated that the network connections shown are exemplary and other means of establishing communications over wide area network 52 may be used.

Preferably, computer-executable instructions stored in a memory, such as hard disk drive 27, and executed by computer 120 embody the illustrated inference engines, including processes 104, 106 (including processes 218, 220) and engines 110, 116. Moreover, computer 20 is suitably embodies computer 120.

In operation, system 100 transforms disparate data for use in rendering an underwriting decision involving a potentially insurable risk. The processes 104, 106, for example, receive data, which is in a plurality of formats, from a plurality of sources (i.e., external data 102). At least process 106 extracts the data and converts it into one or more standard formats. The heuristic engine 110 then filters the converted data by relevancy to the underwriting decision to be rendered. The consolidation and presentation engine 116 generates presentable knowledge from the converted data, and presents the knowledge to a decision-making entity for rendering the underwriting decision. By monitoring one or more actions on the presented knowledge by the decision-making entity, optimization process 122 can adjust one or more steps as a function of the monitored actions.

Alternatively, in operation, system 100 structures and transforms disparate data for use in rendering an underwriting decision involving a potentially insurable risk. The processes 104, 106, for example, retrieve data from a first database, such as database 102, and transform the retrieved data into domain-specific information. Once transformed, the information, which relates to the potentially insurable risk, is stored in a second database, such as staging area repository 108. The heuristic engine 110 defines one or more relevancy factors as a function of the underwriting decision to be rendered and assigns at least one of the relevancy factors to at least a portion of the information stored in the second database. Additionally, consolidation and presentation engine 116 providing an output of the second database with the assigned relevancy factors to a decision-making entity for rendering the underwriting decision.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Embodiments of the invention may be implemented with computer-executable instructions. The computer-executable instructions may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. A method of structuring and transforming disparate data for use in rendering a decision involving a potentially insurable applicant, said method comprising:
    retrieving, by a computer, data from a first database, said retrieved data relating to the applicant; and
    executing, by the computer, computer-executable instructions for:
        transforming the retrieved data into domain-specific information, said domain-specific information relating to insurability of the applicant;
        storing the transformed domain-specific information in a second database;
        defining one or more relevancy factors as a function of the decision to be rendered involving the applicant;
        assigning at least one of the relevancy factors to at least a portion of the transformed domain-specific information stored in the second database;
        processing the transformed domain-specific information as a function of the assigned relevancy factors;
        providing an output comprising the assigned relevancy factors to an underwriter for use in rendering the decision involving the applicant, wherein the processing, by the computer, comprises at least one of: ant colony optimization, a heuristic algorithm, network theory, predictive modeling, deterministic chaos, behavioral economics, fractal geometry, and cellular automata;
        monitoring one or more actions on the provided output by the underwriter in rendering the decision;
        generating feedback as a function of the monitored actions;
        adjusting, by the computer, at least one of said transforming, defining, assigning, and processing the transformed domain-specific information subsequent to providing the feedback to the underwriter; and
        presenting an updated output to the underwriter based on the feedback.

2. The method of claim 1, wherein transforming the retrieved data into domain-specific information comprises executing a domain-specific Extract, Transform, Load (ETL) process to extract the retrieved data and convert the extracted data into one or more standard formats.

3. The method of claim 1, wherein the data stored in the first database comprises one or more of the following types of data: applicant-provided data, electronic medical records data, electronic health records data, continuity of care records data, prescription data, other medical sources data, financial sources data, motor vehicle records data, and other non-medical sources data.

4. The method of claim 1, wherein assigning the at least one of the relevancy factors comprises executing a heuristic engine on the information stored in the second database to infer risk assessment relationships among the information.

5. The method of claim 1, wherein the retrieved data comprises one or more of the following types of complex data: social network data and datamart data.

6. The method of claim 5, further comprising executing a data mining process on the complex data to identify covariance relationships among the data.

7. The method of claim 6, wherein the data mining process comprises predictive modeling.

8. The method of claim 1, wherein one or more computer-readable media have computer-executable instructions stored thereon for performing the method of claim 1.

9. A system of structuring and transforming disparate data for use in rendering a decision involving a potentially insurable applicant, said system comprising:
    a first database storing data relating to the applicant; and
    a computer configured to execute computer-executable instructions for:
        transforming data retrieved from the first database into domain-specific information, said domain-specific information relating to insurability of the applicant;
        storing the transformed domain-specific information in a second database;
        defining one or more relevancy factors as a function of the decision to be rendered involving the applicant;
        assigning at least one of the relevancy factors to at least a portion of the transformed domain-specific information stored in the second database;

processing the transformed domain-specific information as a function of the assigned relevancy factors;

providing an output comprising the assigned relevancy factors to an underwriter for use in rendering the decision involving the applicant, wherein the processing comprises at least one of: ant colony optimization, a heuristic algorithm, network theory, predictive modeling, deterministic chaos, behavioral economics, fractal geometry, and cellular automata;

monitoring one or more actions on the provided output by the underwriter in rendering the decision;

generating feedback as a function of the monitored actions;

adjusting, by the computer, at least one of said transforming, defining, assigning, and processing the transformed domain-specific information subsequent to providing the feedback to the underwriter; and presenting an updated output to the underwriter based on the feedback.

10. The system of claim 9, wherein transforming the retrieved data into domain-specific information comprises executing a domain-specific Extract, Transform, Load (ETL) process to extract the retrieved data and convert the extracted data into one or more standard formats.

11. The system of claim 9, wherein the data stored in the first database comprises one or more of the following types of data: applicant-provided data, electronic medical records data, electronic health records data, continuity of care records data, prescription data, other medical sources data, financial sources data, motor vehicle records data, and other non-medical sources data.

12. The system of claim 9, wherein assigning the at least one of the relevancy factors comprises executing a heuristic engine on the information stored in the second database to infer risk assessment relationships among the information.

13. The system of claim 9, wherein the data retrieved from the first database comprises one or more of the following types of complex data: social network data and datamart data.

14. The system of claim 13, wherein the computer is further configured to execute computer-executable instructions for executing a data mining process on the complex data to identify covariance relationships among the data.

15. The system of claim 14, wherein the data mining process comprises predictive modeling.

16. A non-transitory computer-readable medium storing computer-executable instructions, which instructions when executed by a computer cause the computer to structure and transform disparate data for use in rendering a decision involving a potentially insurable applicant, said computer-executable instructions comprising:

transforming data relating to the applicant into domain-specific information, said domain-specific information relating to insurability of the applicant;

defining one or more relevancy factors as a function of the decision to be rendered involving the applicant;

assigning at least one of the relevancy factors to at least a portion of the transformed domain-specific information;

processing the transformed domain-specific information as a function of the assigned relevancy factors;

providing an output comprising the assigned relevancy factors to an underwriter for use in rendering the decision involving the applicant, wherein the processing comprises at least one of: ant colony optimization, a heuristic algorithm, network theory, predictive modeling, deterministic chaos, behavioral economics, fractal geometry, and cellular automata;

monitoring one or more actions on the provided output by the underwriter in rendering the decision;

generating feedback as a function of the monitored actions;

adjusting at least one of said transforming, defining, assigning, and processing the transformed domain-specific information subsequent to providing the feedback to the underwriter; and presenting an updated output to the underwriter based on the feedback.

17. The computer-readable medium of claim 16, wherein transforming the retrieved data into domain-specific information comprises executing a domain-specific Extract, Transform, Load (ETL) process to extract the data and convert the extracted data into one or more standard formats.

18. The computer-readable medium of claim 16, wherein the data comprises one or more of the following types of data: applicant-provided data, electronic medical records data, electronic health records data, continuity of care records data, prescription data, other medical sources data, financial sources data, motor vehicle records data, and other non-medical sources data.

19. The computer-readable medium of claim 16, wherein assigning the at least one of the relevancy factors comprises executing a heuristic engine on the transformed domain-specific information to infer risk assessment relationships among the information.

20. The computer-readable medium of claim 16, wherein the data comprises one or more of the following types of complex data: social network data and datamart data.

21. The computer-readable medium of claim 20, wherein the computer-executable instructions further comprise executing a data mining process on the complex data to identify covariance relationships among the data.

22. The computer-readable medium of claim 21, wherein the data mining process comprises predictive modeling.

* * * * *